United States Patent [19]

Bailey

[11] 4,021,918

[45] May 10, 1977

[54] SPRING CLUTCH DENTAL HANDPIECE

[75] Inventor: Ronald L. Bailey, St. Peters, Mo.

[73] Assignee: Young Dental Manufacturing Company, Hazelwood, Mo.

[22] Filed: May 15, 1975

[21] Appl. No.: 577,708

[52] U.S. Cl. .................................................. 32/27
[51] Int. Cl.$^2$ ........................................... A61C 1/10
[58] Field of Search ............. 279/1 SG, 102, 96, 9; 32/26, 27, 57

[56] References Cited

UNITED STATES PATENTS

| 2,105,330 | 1/1938 | Pagenkopf | 279/102 |
|---|---|---|---|
| 2,564,893 | 8/1951 | Gibbons | 379/23 |
| 2,570,570 | 10/1951 | Lee | 279/23 |
| 3,314,153 | 4/1967 | Maurer | 32/27 |

FOREIGN PATENTS OR APPLICATIONS

| 1,072,069 | 9/1954 | France | 32/27 |
|---|---|---|---|

Primary Examiner—Robert Peshock
Attorney, Agent, or Firm—Rogers, Eilers & Howell

[57] ABSTRACT

A dental handpiece including an instrument holder which comprises an integral gear and tube, the tube having a closed-end bore or socket which houses a spiral spring of uniform inside diameter, with a slot being provided in the tube for securing one end of the spring, and with a cap which fits on the end of the tube and aids in securing the spiral spring within the tube bore, and acting to grip and hold a dental instrument within the instrument holder when the holder is stationary and driving the instrument to rotate with the instrument holder by a tightening of the coils of the spring around the instrument. A modification of the disclosure features an instrument holder comprising an integral sleeve and turbine, with the holder having means to hold the turbine and sleeve motionless so as to allow insertion and removal of a dental instrument including a ramp-type bearing sleeve. Other alternate methods of holding the sleeve motionless to allow removal include a rubber bladder with a heel, a lever pin and a locking pin.

15 Claims, 15 Drawing Figures

SPRING CLUTCH DENTAL HANDPIECE

BACKGROUND OF THE INVENTION

1. Field of the Invention

This invention relates to improvements in attachment devices used to secure dental instruments in dental hand pieces. The invention is more particularly concerned with, but not limited to, a spiral spring clutch or chuck with the spiral spring housed within the bur tube, to permit the dental instrument to be inserted or removed therefrom. Whenever the instrument is rotated to unwind the spring, it releases the tool shank, but when the instrumemt is rotated to wind the spring, as when the cutting portion of the instrument engages a working surface, the spring grips the tool shank. The convolutions of the spring are initially in contact with each other, to prevent or minimize end play. The tool shank has a snug fit into the spring, to prevent it from falling out when there is no rotational force exerted by the dental instrument against the spring resistance. The invention is also concerned with means for holding the bur tube motionless when it is used with a turbine power system, so as to allow insertion and removal of the instrument from the bur tube when the turbine is not being powered by compressed air.

2. Prior Art (Spring Clutch Handpiece)

In dental handpieces known to the prior art, spiral springs have been employed to grip the shank of a dental instrument in order for the instrument to rotate with some other component with which the spring was attached. This type of handpiece requires the spring to have both of its ends attached to other parts of the handpiece, so that these parts could be manually adjusted to grip or release a dental instrument shank which was manually inserted in or removed from the handpiece.

The present invention has advantages over that type of arrangement. It comprises a spring installed in the bore of an instrument tube, with one end of the spring lying free within the tube bore. No manual adjustment need be made to prepare the spring for the insertion or removal of the shank of the dental instrument, as the shank is inserted by simply rotating and pushing the shank into the spring, and removed by similarly rotating the shank and pulling it out of the spring. As there are no parts used to secure and to adjust the free end of the spring, manufacturing costs are also reduced.

Tool chucks employing a spring as a gripping device are found in non-analogous art, and furthermore do not provide the precision in rotation that is essential in the operation of a dental instrument. These devices rely on the spring itself to provide assitance in guiding or piloting the tool during its rotation which creates a wobbling effect not suitable for dental work, and also causes the wear of the spring. Such chucks also provide for either the fit of a tapered shank into a spring of uniform inside diameter, or the fit of a cylindrical or tapered shank into a spring with a tapered inside diameter. Consequently, these springs do not have uniform gripping strength along the shank, and may lose gripping power on the shank if the shank is moved downward in the spring, even though the shank body is still within the convolutions in the spring, The tapered nature of these chucks also makes it more difficult for the end of the shank to seat within the chuck and have a proper thrust bearing fit.

The present device employs a spiral spring to grip and retain the dental instrument, but does not employ the spring as a pilot to guide the rotation of the instrument, as the instrument fits snugly within two bores or bearings located at opposite ends of the instrument holder. During operation, these two bores prevent eccentric rotation and are machined so that the spring need not act as a pilot, which eliminates the wobbling effect that spring guidance manifests, and also reduces wear of the spring.

The spring in the present device is of uniform inside diameter, so that it may receive an instrument shank of uniform diameter. This allows the spring to grip the shank whenever part of the shank is within the spring convolutions. Consequently, the instrument holder has the additional safety factor of having the capacity to grip the instrument when, for whatever reason, the instrument shank is not completely inserted within the spring, thus preventing its inadvertent removal into the mouth of the patient. When the instrument is completely inserted, the uniform gripping power of the spring throughout its length around the shank provides for stronger retention than is provided by devices with either a tapered shank or a tapered spring. Also, because neither the shank or spring is tapered, the end of the shank is allowed to sit comfortably in the tube bore so as to have a proper thrust bearing fit.

Other forms of the prior art employing a friction grip method of securing the dental instrument use a collet to secure the instrument. The collet is generally tubular in shape with slots in the tube which open at one end of the tube. This collet can sit in a cylindrical bore having a tapered end within the instrument holder, so that when a force is applied to the other end of the collet as by a threaded nut, the fingers of the collet formed between the slots will be pushed inwardly so as to grip a dental instrument which has been inserted in the instrument holder through the collet. The fingers of the collet are delicate and may be broken easily through shipping or through the use of the device. For example, if a dental instrument is not inserted in the instrument holder and the fingers of the collet are pushed inwardly, they can easily break because they are not met by the resistance of the instrument shank. An opening must be provided at the top of the head of the hand piece so that a wrench can be inserted through the head to tighten or loosen the collet. The collet also has a tendency to slip when the load on the dental instrument increases.

The present invention has advantages over the collet type instrument. It is not necessary to have an extra part such as a wrench to tighten or loosen the dental instrument. It also eliminates the necessity of having openings in the back part of the instrument head where bacteria and saliva can enter the hand piece, making it more aseptic. The problem with slipping is greatly reduced as the spring grip increases as the load on the dental instrument increases, and there is also little problem with the spring breaking through use.

In dental instrument employing turbines as a drive force, the prior art has used devices to allow for the removal of the dental instrument from the instrument tube. These prior art devices have openings in the top of the instrument head to allow for the inserting of a pin or wrench to effect removal of the instrument.

The present turbine operated arrangement device has a ramp type bearing which allows the instrument to be easily inserted in and withdrawn from the tube as it is not necessary to insert any separate component into the top of the dental head, and a more aseptic device is thus provided. Modifications of this device employ a lever pin or a locking pin housed within the instrument holder to hold the tube motionless to allow removal. Another modification employs a rubber bladder that can be pressurized so as to be forced against the turbine in order to hold the tube steady. These modifications also reduce the amount of bacteria that can enter the dental head, and are simple to operate.

DESCRIPTION OF THE PREFERRED EMBODIMENT

Figures 1, 2, 3, 4, 5, 6:
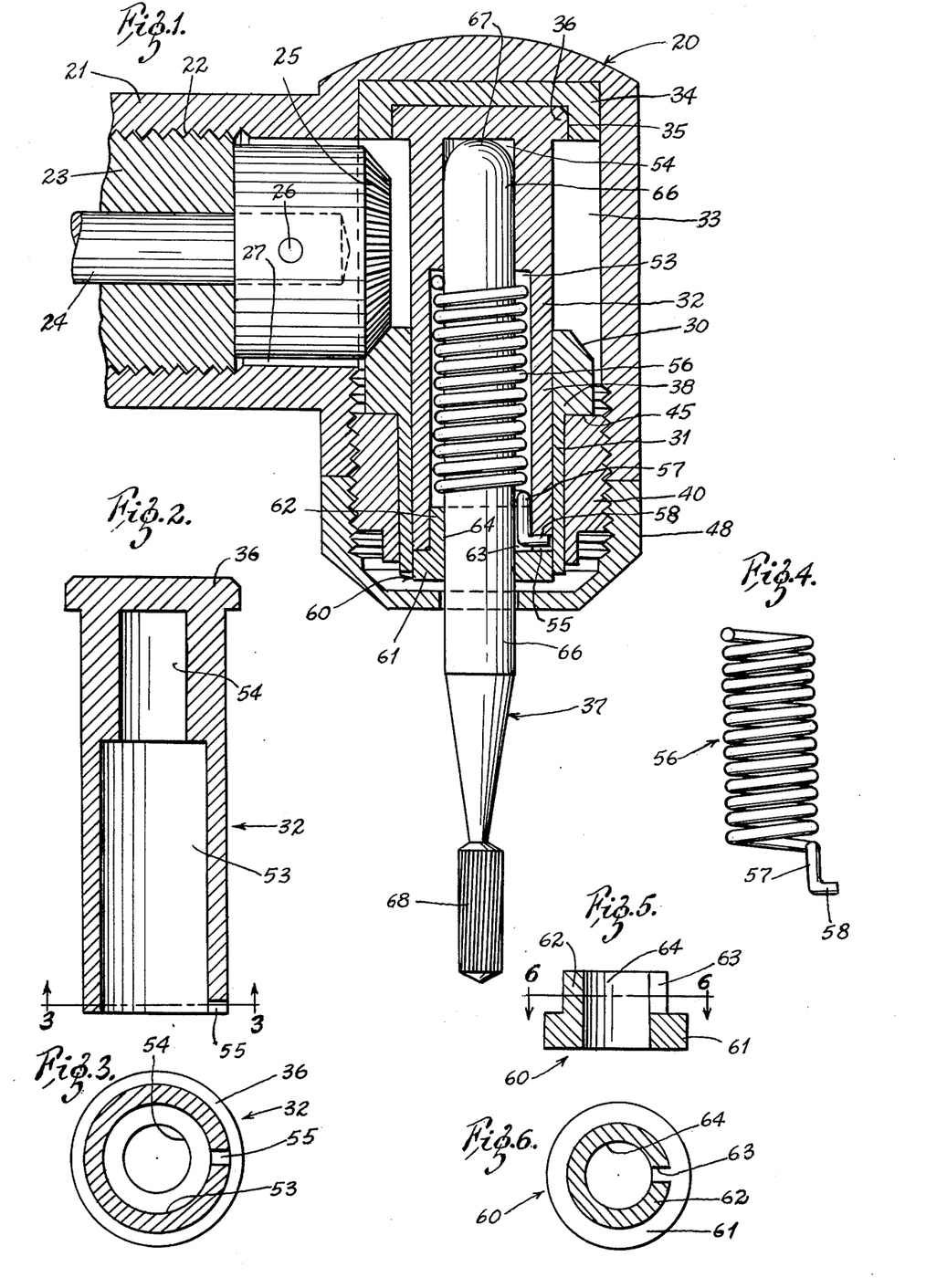
FIG. 1 is a central vertical sectional view of the head of an angle dental handpiece illustrated in accordance with the invention, with a dental bur being shown inserted and retained, and in position to be driven by the rotation of the bur tube.
FIG. 2 is a central vertical sectional view of an instrument tube or bur tube.
FIG. 3 is a bottom sectional view of a bur tube taken on the line 3—3 of FIG. 2.
FIG. 4 is a vertical side view of a spiral spring.
FIG. 5 is a central vertical sectional view of the cap that fits on the end of the instrument tube.
FIG. 6 is a top sectional view of the cap taken on the line 6—6 of FIG. 5.

Referring to FIG. 1, a housing 20 that constitutes the head of the handpiece is provided with a lateral tubular extension 21, internally threaded at 22 so as to receive the externally threaded bearing sleeve 23. The bearing sleeve 23 is adapted to support a drive shaft 24 which extends through the sleeve 23 to a position so that it may be connected to a bevel gear 25 by a pin attachment 26, which may be pressed into place. The bearing sleeve 23 is adapted to confine the gear 25 in the housing 21 and to adjust its position relative to a companion gear to be described. The drive shaft 24 is driven by a motor usually with a flexible shaft connection, not shown.

The housing tubular extension member 21 is provided with a bore 27 of great enough size to allow clearance of the gear 25. The teeth of the gear 25 mesh with the teeth of a gear 30. The gear 30 is formed on an outer sleeve 31 that is secured to the outside of an instrument or bur tube 32 so as to be integral therewith, thus comprising the bur tube assembly 38, the rotation of the gear 30 driving the bur tube 32. The bur tube 32, in turn, is adapted to receive a dental instrument 37, which can be a bur.

The bur tube 32 and the gear 30 secured integrally thereto are rotatably supported in the bore 33 in the head 20. At the top of the head 20, the bore 33 receives a bushing 34 which can be soldered into place. The bushing 34 has a downwardly-facing circular recess 35. This recess acts as a bearing for the circular flange 36 on the upper end of the bur tube 32. There is also an externally threaded bearing sleeve or lower bushing 40 located at the lower end of the housing 20 to rotatably receive the lower end of the bur tube 32. The two bushings 34 and 40 provide stable support for the tube 32.

The threads on the sleeve 40, home on threads in the lower part of the housing 20. When the threads are properly interengaged, the upper end of the sleeve 40 engages a shoulder 45 of the gear 30, to displace it and the bur tube upwardly in such a way that the gear 30 will properly mesh with the gear 25, and also so that the bur tube 32 will rest with its upper end having a proper thrust bearing fit with the downwardly facing recession 35 of the bushing 34. A cap 48 has interior threads that also engage with the bearing sleeve threads so that the cap 48 fits on the lower part of the housing 20. The cap 48 has a cylindrical opening at its bottom. When the cap 48 is drawn tightly onto the threads, it acts also as a lock-nut for the bearing sleeve 40 in the head 20. The sleeve 40 and cap 48 can also be glued together so as to form one piece.

The cylindrically shaped bur tube 32 as shown in FIG. 1 and more specifically in FIG. 2 has a cylindrical concentric bore 53. The bur tube also has a cylindrical counterbore 54 which intersects the bore 53, and is concentric with the bore 53 and the bur tube 32, and has a smaller diameter than the bore 53. The counterbore is designed to snugly receive the shank 66 of the dental instrument 37, but yet to allow it to be readily removed by hand. The bur tube 32 has a radial notch 55 located at the bottom of the tube, which extends from the outside of the bur tube wall through to the bore 53.

The bur tube bore 53 is open at the lower end of the bur tube 32 and is of such a diameter as to loosely receive a spiral spring 56, as shown in FIGS. 1 and 4. The spiral spring 56 has a length which is slightly less than the depth of the bore 53. The spring 5 has a uniform inside and outside diameter designed to telescopically receive the shank 66 of the dental bur 37, which has a uniform diameter. The end of the spring near the opening in the bur tube has a straight segment 57 which extends downwardly in the bore and turns outwardly into a radical segment 58, so that the segment 58 fits snugly in the radial notch 55 of the bur tube 32, and is secured therein. The other end of the spring is unattached and lies free in the bore 53 of the bur tube 32.

A cap 60, as shown in FIG. 1 and more specifically in FIGS. 5 and 6, has a cylindrical flange 61 and a cylindrical projection 62 extending upwardly from the larger cylindrical flange 61. The cylindrical projection 62 has a slot 63 extending from the top to the bottom of the cylindrical section 62, and of such a width as to snugly receive the downwardly-extending segment 57 of the spiral spring 56. A bore 64 is formed by the inside diameters of the cylinders 62 and 61, and is designed to telescopically receive the shank 66 of the instrument. The cap 60 is designed so that the outer wall of the cylinder 62 may be press-fitted into the bur tube bore 53, so that the slot 63 of the cap will be aligned with the slot 55 of the bur tube wall.

A dental instrument such as a dental bur 37, with a cylindrically-shaped shank 66 having a uniform diameter, and a rounded end 67, is designed to telescopically fit within the bur tube counterbore 54 and the cap bore 64. The counterbore 54 and cap bore 64 act as bearings and as pilots to properly support the dental bur 37 during use. The dental bur 37 extends from the bur tube bore 54 through the opening in the cap 48 so that the cutting portion 68 of the dental bur is exposed.

Figure 10:
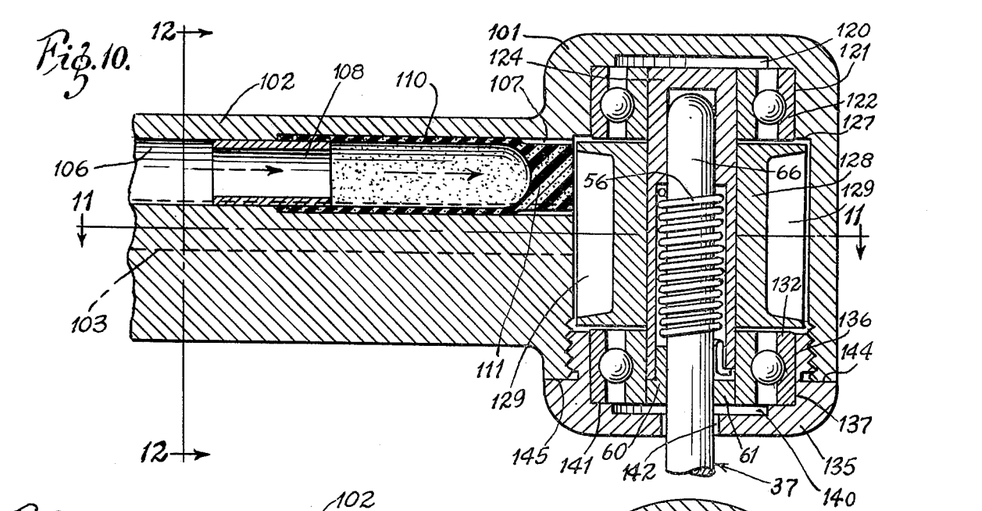
FIG. 10 is a central vertical sectional view of the head of an angle dental handpiece illustrated in accordance with a modification of the invention, with a rubber bladder.
Figures 11, 12, 13:
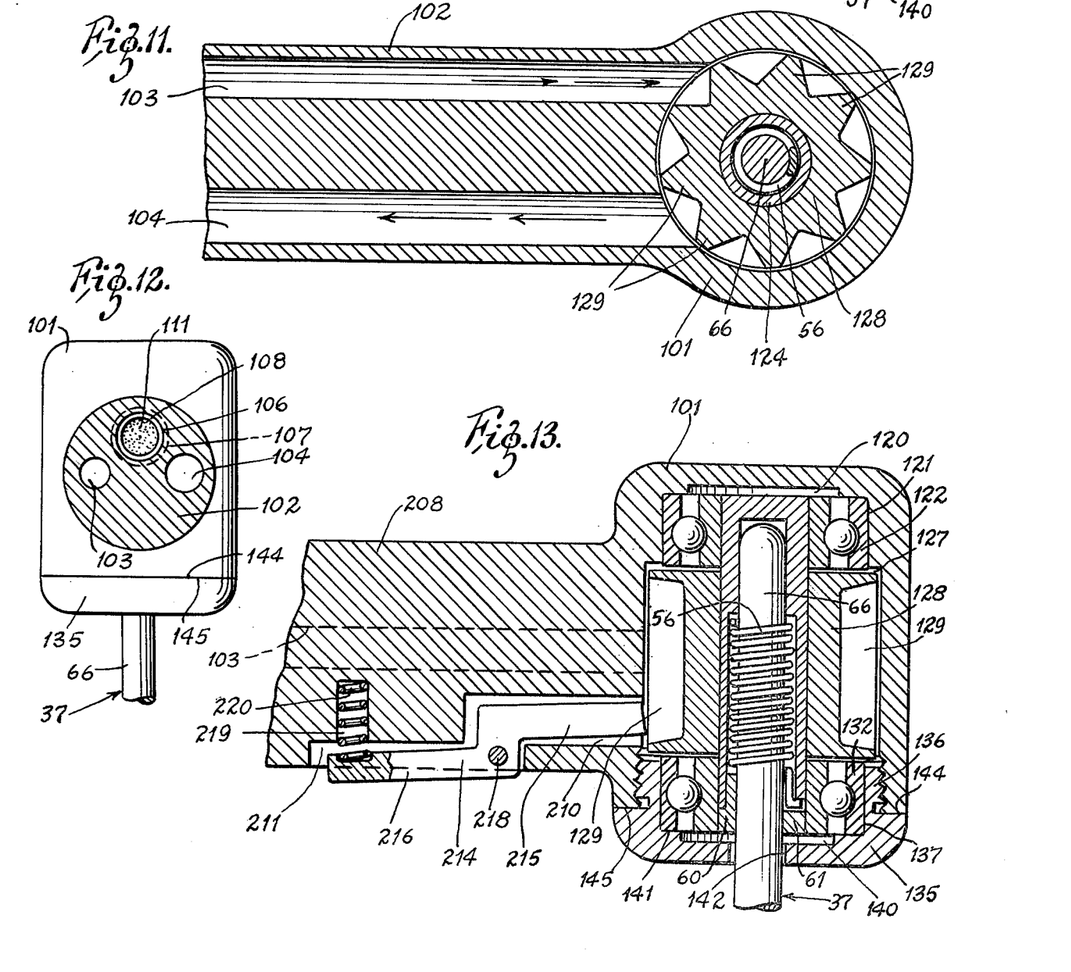
FIG. 11 is a top sectional view taken on line 11—11 of FIG. 10.
FIG. 12 is a reduced scale end sectional view on the line 12—12 of FIG. 10.
FIG. 13 is a central vertical sectional view of the head of an angle dental handpiece illustrated in accordance with a modification of the invention; illustrating a lever pin.

The modifications according to FIGS. 7 through 14 in no way affect the functions or operative principles of the improvements as hereinabove set forth and are concerned solely with alternate means for driving the bur tube and with alternate means for holding the bur tube motionless in order to allow inserting and removal of the dental instrument. Referring to FIG. 10, a housing 101 that constitutes the head of the hand piece is provided with a lateral tubular extension 102. As shown in FIG. 11 and in FIG. 12, the extension 102 has a bore 103 which acts as an inlet for pressurized air that provides thrust for a turbine yet to be described. The extension 102 also has a second bore 104 which acts as an outlet for exhaust for the pressurized air supplied to the turbine.

The extension 102 also has a cylindrical bore 106 located near the top of the extension 102 and a larger concentric counterbore 107 which intersects the bore 106 (FIGS. 10 and 12). A tube 108 is telescopically received and firmly attached as by a press fit within the bore 106 with one end of the tube 108 extending into the counterbore 107. A cylindrically shaped rubber bladder 110 is telescopically received within the counterbore 107 with its open end telescopically receiving the end of the tube 108 and being firmly attached thereto as by a strong glue. The bladder 110 has a heel 111 of smaller diameter at the closed end of the bladder. This heel acts as a braking device for a turbine yet to be described.

The head 101 has a circular recess 120 located at the top of the head 101. A larger concentric counterbore 121 intersects the recess 120. The counterbore 121 telescopically receives a ball bearing sleeve 122. The inner wall of the bearing sleeve 122 is firmly attached to the outer wall of a cylindrical bur tube 124 as by a press fit so as to be integral therewith, with the top end of the bur tube 124 aligned with the top end of the bearing 122. The head 101 also has a bore 127 large enough to allow rotation of a turbine wheel 128. The turbine 128 has blades 129 and a central bore allowing it to telescopically receive and be firmly attached to the outside of the bur tube 124 as by a press fit. The location of the turbine 128 within the bore 127 is such that the circumferential perimeter of the turbine is a slight distance from the end of the rubber heel 111, the end of the inlet 103, and the end of the exhaust 104. Other than the lack of a flange at the top of the tube, the bur tube 124 is identical in all other respects to the bur tube 32 described previously in the gear type assembly, and illustrated in FIGS. 1 and 2. The bur tube 124 likewise houses a spring 56 as is shown in FIG. 4. A cap 60 (FIG. 5) also fits on the end of the bur tube 124 and aids in securing the spring 56 as previously described.

A second ball bearing sleeve 132 telescopically receives the lower part of the instrument tube 124 and the flange 61 of the cap 60 and is firmly attached to them as by a press fit. A cap 135 has an externally threaded projection 136. The cap 135 also has a cylindrical bore 137 which telescopically receives the bearing sleeve 132. The cap 135 has a counterbore 140 which intersects the bore 137 forming a ledge 141 upon which the outer part of the bearing sleeve 132 rests. Another bore 142 passes through the bottom wall of the cap 135 allowing the instrument shank 66 to extend through it, exposing the cutting portion 68 of the instrument 37. The cap 135 has an outer ledge 144 which fits flush against the lower rim 145 of the head 102.

The modification in FIG. 13 features another method for holding the turbine motionless so that the dental bur may be inserted and removed. The head 101 has a tubular extension 208. There is also an air inlet 103 which supplies air to the turbine and an air exhaust outlet 104 which allows for the exhaust and reduction of pressurized air from the bore 127 as described in the discussion of the bladder-type brake. The tubular extension 208 has a recess 211 located on its bottom side. A bore 210 is located above the recess 211 with the lower left end of the bore 210 intersecting the upper right end of the recess 211. A locking lever 214 is housed within the bore 210 and the recess 211 with the upper end of the lever 215 being housed within the bore 210 and the lower end of the lever 216 being located in the recess 211. A pin 218 passes through the outside of the tubular extension 208 through the locking lever 214 holding the lever in place. The tubular extension 208 also has a circular bore 219 which intersects the recess 211. The circular bore 219 houses a spiral spring 220 with one end of the spiral spring lying free in the bore 219 and the other end of the spiral spring 220 located in a circular recess in the upper surface of the trigger portion 216. A protective sleeve can be provided on the exterior of the tubular extension 208 to prevent inadvertent operation.

The end of the lever portion 215 is slightly slanted from upper left to lower right so that it will have uniform contact with the circumferential perimeter of the turbine 128 when the lever 214 is rocked. The components contained within the head 101 are the same as those described in the discussion of the rubber bladder modification.

Figures 7, 8, 9, 14, 15:
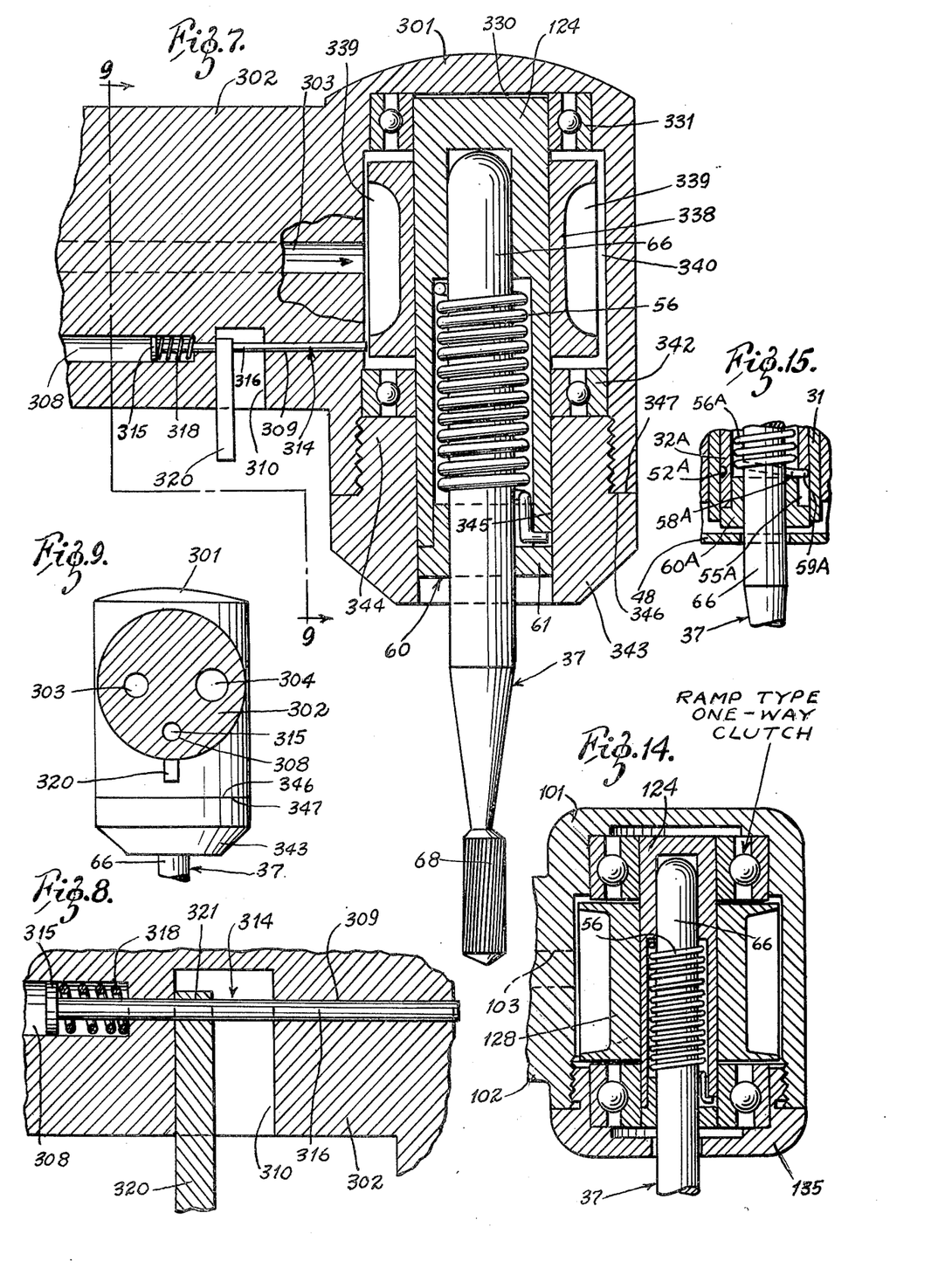
FIG. 7 is a central vertical sectional view of the head of an angle dental hand piece illustrated in accordance with a modification of the invention, with a dental bur being shown inserted and retained, and in position to be driven by the rotation of the bur tube.
FIG. 8 is an enlarged view, partly in section, of the locking pin shown in FIG. 7.
FIG. 9 is a section on the line 9—9 of FIG. 7.
FIG. 14 is a central vertical sectional view of the head of an angle dental handpiece illustrated in accordance with a modification of the invention, illustrating a one-way or ramp-type ball bearing sleeve.
FIG. 15 is a central vertical sectional view of the lower part of a bur tube illustrated in accordance with a modification of the invention.

Another modification used to hold the turbine 128 motionless so as to allow insertion and removal of the instrument from the bur tube 124 is shown in FIG. 14. A ramp type ball bearing sleeve or one-way free-wheeling clutch, as shown in FIG. 14, is firmly attached to the outside of the bur tube 124 as by a press fit. It is self-locking when the bur tube 124 and turbine 128 are rotated in a direction reverse of the drive rotation, but rotatable in the drive direction. The rest of the components within the head 101 are the same as described and illustrated in the discussion of the bladder brake and the lever brake in conjunction with FIGS. 10 and 13. Obviously this modification also has an air inlet 103 and an exhaust 104 as previously described, and as illustrated in FIG. 11, only the air inlet being shown in FIG. 14. It is noted that in this modification there is no trigger, pin or rubber bladder or any other braking device contained in the tubular extension 102.

Another modification used to facilitate the insertion and removal of the dental instrument from the bur tube is shown in FIGS. 7, 8 and 9. Referring to FIG. 7, a housing 301 that constitutes the head of the hand piece is provided with a lateral tubular extension 302, which has a circular bore 303 extending through the tubular extension and which acts as an inlet for air pressure to power a turbine yet to be described. The extension 302 also has a tubular bore 304 (FIG. 9) which extends to the right end of the tubular extension 302 with its opening near a turbine yet to be described. The bore 304 acts as an exhaust tube in a similar manner as hereinbefore discussed for the exhaust tube of the other modifications.

The tubular extension 302 has a circular bore 308 which is parallel to the bores 303 and 304, and located beneath them. The bore 308 extends from the left to the right of the extension 302 until it is intersected by a smaller concentric bore 309. The bore 309 extends to the right end of the tubular extension 302 opening at a point near a turbine yet to be described. A bore 310 extends from an opening on the bottom side of the extension 302 to a point above the bore 309, and intersects the bore 309.

A pin 314 has a head 315 and a shank 316. The head 315 of the pin 314 is telescopically received by the bore 308 so that it may slide within the bore 308. The pin shank 316 is telescopically received by the bore 309 so as to be capable of sliding therein.

A spiral spring 318 is housed within a bore 308, with one end of the spring in contact with the right side of the pin head 315, the other end of the spring in contact with the right end of the bore 308 and with the pin shank 316 passing through the spring 318. A handle 320 extends into the bore 310. The handle 320 has a circular bore 321 as shown in FIG. 8 which telescopically receives the shank 316 of the pin 314 and is firmly attached thereto as by a press fit. The bottom end of the handle 320 extends below the tubular extension 302. By pushing the handle 320 to the right, the pin 314 can likewise be moved to the right. A protecting sleeve can be provided on the exterior of the tubular extension 302 to prevent inadvertent operation.

The head 301 has a circular recess 330 located near the top of the head which telescopically receives a combination thrust and radial ball bearing 331. The inner race of the ball bearing 331 is firmly attached to the outer wall of the cylindrical bur tube 12 as by a press fit so as to be integral therewith. The top end of the bur tube is held by the bearing out of frictional contact with the housing 301.

A turbine wheel 338 has blades 339, and is firmly attached to the outside of the instrument tube 124 as by a press fit so as to be integral therewith. The turbine 338 may rotate freely within the bore 340 of the head 301. A ball bearing 342 has its inner race attached to the bur tube 124 as by a press fit so as to be integral therewith, at a point below the turbine 338. The outer race of the bearing 342 is telescopically received by the bore 340.

The bur tube 124 is identical to those described in the rubber bladder, lever pin and ramp type modifications, and shown in FIGS. 10, 13 and 14. The bur tube houses a spring 56 (FIG. 4) and has a cap 60 (FIG. 5) secured to its end as previously described.

A cap 343 has an externally-threaded projection 344 and a cylindrical bore 345. The lower end of the bur tube 124 and the flange 61 of the cap 60 are telescopically received by the bore 345 of the cap 343 so as to be rotatable therein. The threads on the projection 344 home with the internal threads located at the bottom of the head 301 so that the cap 343 may be threaded into the lower part of the head 301. With the cap 343 in proper position, the top of the projection 344 presses against the bottom of the ball bearing sleeve 342 so as to obtain proper thrust bearing fit of the bur tube 124 and bearing sleeve 331 with the recess 330. The outer ledge 346 of the cap 343 seats against the bottom rim 347 of the head 301. The cap 343, the recess 330 and bearing sleeves 331 and 342 provide stable support for the tube 124. A dental instrument 37 extends from within the bur tube 124 through the cap bore 345 so that its cutting portion 68 is exposed.

Another modification of the invention is shown in FIG. 15. The bur tube 32A has a longitudinal slot 55A in its wall. The segment 58A of the spring 56A can slide upward through the slot as the spring is installed in the bur tube. The end of the portion 59A of the spring is arcuately bent so that it fits into the circumferential groove 52A on the outside of the bur tube. The gear sleeve 31 acts to keep the end of the spring 59A in the groove 52A. The cap 60A need not have a slot, and can be press fit into the bottom of the bur tube, thus holding the end of the spring 56A in place.

Operation

To assemble the head, the bushing 34 is secured in place. The bur tube assembly 38 is first assembled, as by a press or ordered fit of the bur tube 32 into the gear sleeve 31 so that they are firmly attached together for present purposes. This subassembly 38 is inserted into the head 20 from the bottom end until the flange 36 seats in the recess 35 of the bushing 34.

The cap 38 can be pre-fit with the collar 40 by threading the cap 48 on the projected threads of the collar 40 a predetermined distance, with the cap 48 being secured to the collar 40 by an adhering substance, such as a strong epoxy glue. With the cap 48 and the collar 40 secured together, the threaded collar 40 is then placed around the sleeve 31 and threaded into the head so as to engage the shoulder 45 on the gear 30 and urge the subassembly 38 up to establish proper thrust bearing fit of the bur tube. The pre-fit combination of the collar 40 and the cap 48 is such that the seating of the flange 36 in the recess 35 occurs simultaneously with the contact of the top portion of the cap with the bottom portion of the head. In the foregoing assembly, there are only two parts to be separately attached to the head. Of course, if it is desired, the collar 40 may be separate from the cap 48, and the collar 40 may be threaded into the head first so that the subassembly 38 is urged upwardly to obtain proper thrust bearing fit of the bur tube. Then the cap 48 may be threaded onto the collar 40.

When the components are assembled as described above, the dental instrument or bur 37 may be inserted into the instrument or bur tube 32, by pushing the bur inwardly through the cap bore 64 until the rounded end 67 of the bur shank 66 contacts the spiral spring 56, whose end segment 58 is attached in the slots 55 of the bur tube 32 and 63 of the cap 60, and whose other end is free in the bur tube bore 53. The shank 66, being of uniform diameter, with its rounded end 67 in contact with the spring 56, is rotated by the fingers in a direction to unwind the spring, the friction between the shank 66 and the spring 56 turning the spring convolutions, causing the inside diameter of the spring 56 to slightly increase. The shank 66 is pushed inwardly into the bur tube bore 53 as the rotation is continued, until the rounded end 67 of the shank 66 contacts the end wall of the counterbore 54, and the shank fits snugly in the counterbore 54 and cap bore 64.

After the shank 66 rotation ceases, the uniform inside diameter of the spring 56 contracts, causing the spring convolutions to grip the shank 66 to uniform diameter, and to prevent its pure vertical motion within the bur tube. It can be seen, that since the inside diameter of the spring 56 and the diameter of the dental shank 66 are both uniform, the shank 66 will be gripped regardless of its position within the bur tube bore 53 as long as the shank is within the spring convolutions.

The spring convolutions are initially very close together, and indeed in contact with one another, so that the initial gripping of the bur shank results mainly from the frictional engagement due to the sizes of the interfitting parts. Typically a bur shank can have an o.d. 0.0625–0.0628 inch and the coil spring an i.d. of 0.0620–0.0624 inch. By making the coils close together, end play is minimized between the bur shank and the spring, as loose convolutions may permit axial movement of the bur shank upon any upward pull on the head. This movement occurs until the convolutions do contact. By having them together initially, this is avoided. In a dental handpiece this means that the user does not find the dental tool moving axially in the handpiece when the handpiece is drawn upwardly on a tooth that offers some resistance to the movement.

When the bur tube 32 is rotated in a direction opposite that of the insertion rotation, any resistance met by the cutting portion 68 of the bur 65 will increase the friction between the shank 66 and the spring 56 convolutions, and turn the spring so that the grip of the spring 56 is increased and is firm enough to transmit the power of the bur tube rotation and cause the dental bur 65 to rotate in unison with the bur tube 32. It should be noted that the direction of the insertion rotation and drive rotation for the spring are dependent upon the direction of the spiral in the spring 56.

The bur tube counterbore 54 and the cap bore 64 both fit snugly around the shank 66 and serve as stabilizers in acting as pilots to guide the dental bur 37 operation, keeping it from wobbling or bouncing within the bur tube 32. Because of the snug fit of the shank 66 in the counterbore 54 and the cap bore 64, the spring 56 need not act as a pilot or guide.

When the bur tube 32 is stationary, the bur 37 may be removed by rotating it in the same direction as the insertion rotation, thus causing the inside diameter of the spring 56 to slightly increase and decrease the grip of the spring 56 on the instrument shank 66, so that the instrument can be removed by continuing the rotation and pulling the instrument downward.

With regard to the modification shown in FIGS. 10, 11 and 12, the operation is as follows. To assemble the head, the bur tube 124 is first assembled with the bearing sleeves 122 and 132, and the turbine 128 as by a press or ordered fit of the bur tube 124 into the bearing sleeve 132, the turbine 128, and the bearing sleeve 122 so that they are firmly attached together for present purposes. This subassembly is then inserted into the head 101 from the bottom end until the bearing sleeve 122 seats in the counterbore 121 with the top of the sleeve 122 in contact with the top outer ledge of the counter bore 121. The cap 135 can then be threaded onto the threads in the lower part of the housing 101. As the cap 135 is threaded onto the head 101 the cap telescopically receives the lower bearing sleeve 132 and urges it upwardly so that the contacting of the outer ledge of the cap 135 with the bottom ledge of the head 101 occurs simultaneously with the contact of the top of the bearing 122 with the top of the counterbore 121. In the foregoing assembly there are only two parts to be separately attached to the head.

When the components are assembled as described above, the instrument 37 can be inserted into the instrument tube 124. In order to hold the turbine 128 and the instrument tube 124 motionless so that the instrument 37 can be inserted, presurized air or water passes through the bore 106 in the extension 102. The flow of the air or water can be controlled by a foot pedal. The air or water is supplid from a source and through tubes that are used customarily to cleanse the mouth and teeth in dental operations. This air or water passes through the tube 108 and into the rubber bladder 110. The pressure of the air or water on the interior surface of the bladder operates to push the heel 111 forward so that it presses firmly against the upper exterior surface of the turbine 128.

With the turbine 128 and instrument tube 124 held motionless relative to the head 101, the instrument 37 may be inserted into the instrument tube by pushing the instrument upward and rotating it so that the shank 66 can pass through the convolutions of the spring 56 and contact the top of the instrument tube counterbore 54. After the instrument 37 is inserted, it is gripped by the spring convolutions which prevent the pure vertical motion of the shank 66 within the instrument tube as previously described in the gear type assembly operation. If the rubber heel 111 were not used to hold the turbine 128 and the bur tube 124 motionless, the insertion rotation of the shank 67 would not unwind the spring 56. Consequently, the instrument 37 could not be inserted into the bur tube 124. After the instrument 37 has been installed in the instrument tube 124, the air or water pressure inside the bladder 110 may be reduced to allow the elasticity of the bladder to pull the heel 111 back away from the turbine 128, so as not to interfere with the rotation of the turbine within the bore 127.

Ater the rubber heel 111 is withdrawn, pressurized air is supplied through the air inlet 103 and exist through the inlet opening in the head 101 striking the turbine blades 129. The flow of the pressurized air against the turbine blades causes the turbine 128 and also the instrument tube 124 to rotate. The instrument tube 124 rotation is transferred to the instrument shank 66 through the gripping action of the spring 56. The rotation direction of the turbine and bur tube relative to the dental instrument 37 is opposite that of the instrument's insertion rotation relative to the bur tube. Any resistance met by the cutting portion of the instrument 37 will therefore increase the friction grip of the spring around the shank as described previously in the operation of the gear type assembly.

The bore 104 acts as an exhaust outlet permitting removal of the pressurized air from the bore 127 of the head 101. The removal of the air through the exhaust 104 allows a pressure differential to be maintained between the air inlet 103 and the bore 127, thus allowing for the proper functioning of the turbine 128.

When the air flow from the inlet 103 is shut off, the turbine 128 will cease rotating. In order to remove the instrument 37, pressurized air or water is again supplied through the bore 106 and tube 108 into the rubber bladder 110. The expansion of the bladder again causes the rubber heel 111 to press forward against the exterior of the turbine 128. With the turbine and the instrument tube held motionless, the instrument may be removed by twisting it in the same direction as the insertion rotation and pulling the instrument downward while continuing the rotation until it is removed from the instrument tube 125. If the rubber heel did not hold the turbine 128 and bur tube 125 motionless, the twisting of the instrument 37 would only cause the turbine, and the bur tube to rotate. The spring 56 could not unwind so as to loosen its grip on the instrument shank, and the instrument could not be removed from the bur tube. As can be seen, the use of the rubber bladder 110 to allow for the insertion and removval of the instrument does not create a need for openings in the head 101, thr. through which saliva and bacteria from the mouth might enter the hand piece.

The instrument tube counterbore 54 and the cap bore 64 both fit snugly around the shank 66 and serve as stabilizers in acting as pilots to guide the dental bur 37, keeping it from wobbling or bouncing within the instrument tube 124. Because of the snug fit of the shank 66 in the counterbore 54 and the cap bore 64, the spring 56 need not act as a pilot or guide.

The modification shown in FIG. 13 operates in the following manner. In order to insert the dental instrument 37 into the bur tube 124, the turbine 128 and the bur tube 124 are held motionless by the locking lever 214. This is done by pressing upward with a thumb or finger on the bottom of the portion 216 of the lever 214. When the portion 216 is pushed upward, the other lever portion 215 is rotated downward so that its end contacts the exterior surface of the turbine 128.

With the end of the lever portion 215 pressing against the outer surface of the turbine, the turbine and the bur tube are held motionless. Because the bur tube 124 is held still, the insertion rotation of the instrument does not cause the tube 124 and turbine to rotate. The instrument 37 can, therefore, be inserted as described in previous operations, as the insertion rotation of the instrument caused the spring 56 to expand to allow the instrument shank 66 to pass through the spring convolutions. After the instrument 37 is inserted in the bur tube 124, the thumb or finger pressure on the portion 216 of the lever 214 can be released, allowing the force of the spring 220 to push the lever portion 216 downward, causing the end of the other level portion 215 to rotate upward away from the exterior of the turbine 128.

With the end of the lever portion 215 rotated away from the turbine 128, the turbine can rotate without interference in the bore 127 of the head 101. Air passing through the inlet 103 supplies the driving force for the turbine which drives the dental instrument's rotation. The air pressure within the bore 127 is released through the exhaust tube 104 so that the turbine can function properly.

When the air supply through the inlet 103 is shut off, the rotation of the turbine 128 ceases. To remove the dental instrument 37 from the bur tube 124 after rotation ceases, the bottom of the lever portion 215 is again pressed upward causing the end of the lever portion 215 to once again contact the exterior surface of the turbine 128. If the turbine and bur tube 124 were not held still by the lever 214, any attempt to rotate the instrument 37 to remove the pin would simply cause the turbine and bur tube to also rotate, as there is no other element in the hand piece to prevent the rotation of the turbine, and the grip of the spring 56 around the shank 66 would prevent the removal of the instrument. However, with the turbine and bur tube held motionless, the dental instrument can be rotated in the same direction as the insertion rotation and pulled downwardly, causing the spring 56 to expand and loosen its grip so that the instrument can be removed. After the instrument is removed, the pressure against the bottom of the lever portion 216 can be released, so that the spring 220 presses the lever portion 216 downward, thus causing the end of the lever portion 215 to rotate away from the turbine surface.

The modification shown in FIG. 14 employing a ramp type ball bearing sleeve also operates to prevent the turbine and bur tube from rotating so that the dental instrument can be inserted into and removed from the bur tube. The ramp type ball bearing sleeve has its inner wall firmly attached to the outer surface of the bur tube 124. The ramp type ball bearing is rotatable in the direction of the turbine 128 rotation when the turbine is driven by the air pressure from the inlet 103. However, the ramp bearing will not rotate in the reverse direction. Consequently, when the instrument 37 is inserted into the bur tube and rotated in a direction opposite that of the ramp bearing rotation, the bur tube 124 will remain stationary so that the spring 56 convolutions will be expanded to permit the insertion of the instrument. After the instrument is installed, pressurized air may be supplied from the inlet 103 causing the turbine 128, bur tube 124 and dental instrument 37 to rotate. The air pressure within the bore 127 is released through the exhaust tube 104, allowing pressure differential to be maintained between the inlet 103 and bore 127.

After the air flow through the inlet 103 is shut off, the instrument 37 can be removed from the bur tube 124. This is done by pulling the instrument downward while rotating it in a direction opposite that of the ramp bearing rotation, so that the ramp bearing prevents the bur tube 124 from rotating and thus allows the spring 56 to expand and release its grip on the instrument 37, allowing its removal. The use of the ramp bearing to allow for the insertion and removal of the dental instrument causes no need for additional openings in the head 101 or the tubular extension 102 through which germs and saliva could enter the hand piece.

The modification of FIGS. 7, 8 and 9 employs a locking pin which operates to hold the turbine and bur tube motionless to allow for insertion and removal of the dental instrument. When there is no air flow through the air inlet 303 causing the turbine to rotate, the handle 320 which is firmly attached to the pin 314 may be pushed forward by a thumb or finger. The movement of the handle 320 forward forces the end of the pin shank 316 forward so that it contacts the bottom exterior surface of the turbine 338. The force of the end of the pin shank 309 against the turbine holds the turbine 338 and bur tube 124 motionless relative to the head 301 so that the dental bur 37 can be inserted. The bur 37 is inserted and rotated so as to expand the convolutions of the spring 56, allowing the shank 66 of the instrument to pass through the convolutions. After the instrument 37 is inserted into the bur tube 124, the handle 320 can be released, causing the force of the spring 318 against the pin head 315 to force the end of the pin shank 309 away from the turbine surface so that the turbine can rotate freely within the bore 340.

Pressurized air supplied through the inlet 303 operates to cause the turbine 338 to rotate, thus causing the bur tube 124 and dental instrument 37 to rotate in unison with the turbine. The pressurized air contained within the bore 340 in the head 301 is allowed to escape through the exhaust tube 304. Consequently, a pressure differential is maintained between the air inlet 303 and the bore 340, so that the turbine 338 is allowed to function properly.

After the air supply through the inlet 303 has been shut off, and the turbine 338 has ceased to rotate, the handle 320 can again be pushed forward so that the end of the pin shank 316 is also pushed forward so as to push against the bottom of the turbine 338, holding it still. With the turbine 338 and instrument tube 124 held motionless, the dental instrument 37 may be removed by rotating it in the same direction as the insertion rotation and pulling it downward and out of the bur tube. Because of the close telescopic fit of the pin shank 316 in the bore 309, germs and saliva are prevented from entering the head 301 by way of the opening 310.

The modification of FIG. 15 allows for spring operation which permits insertion and gripping of the tool as previously described. The sleeve 31 and cap 60A keep the end portions 58A and 59A of the spring fixed. This modification is much easier to manufacture than the other type of spring and bur tube combination.

Various changes and modifications may be made within this invention as will be readily apparent to those skilled in the art. Such changes and modifications are within the scope and teaching of this invention as defined by the claims appended hereto.

What is claimed is:

1. In a dental handpiece for use with a rotary dental instrument having a cylindrical shank of uniform diameter: a housing having a cavity extending thereinto through an opening in a wall thereof; an instrument tube rotatably mounted in the housing and having an open end and a closed end, the tube being disposed to present its open end toward the opening of the housing whereby an instrument may be inserted through the opening of the housing and into the tube; bearing means in the housing to rotatably engage the tube at spaced points therealong; drive means in the housing to rotate the tube in said bearing means; the instrument tube having a reduced inside diameter adjacent its closed end to receive and snugly hold an instrument, and a larger inside diameter below that reduced diameter; a spiral spring in the larger inside diameter portion having a normal uniform inside diameter over an extended axial part of the spring that is slightly less than the outside diameter of the shank; means to secure the end of the spring inside the tube toward the open end thereof, its other end extending inwardly of the tube and lying within the tube, the spring terminating short of the closed end of the tube, whereby the instrument shank can be projected through the spring and be received in the said closed end of the tube, the spiral spring comprising means to grip the shank throughout the axial distance of uniform inside diameter to hold the instrument in the tube when the drive means is inoperative, and being adapted to grip the shank throughout the said axial distance when the tube is rotated in one direction; a member adjacent the open end of the tube having an opening to receive and stabilize the shank of the instrument.

2. The structure of claim 1 wherein the coils of the spring are initially in at least substantial contact with each other to restrict axial movement of the shank in the spring.

3. The structure of claim 1, the last-named member including a cap having a hole therethrough coaxial with the spring and of a diameter to receive and stabilize the shank and to seal thereagainst.

4. The structure of claim 1 with braking means operable to prevent rotation of the tube in at least one direction.

5. The structure in claim 1 including a turbine firmly attached to the instrument tube and a braking mechanism comprising contact means to contact the turbine to hold the instrument tube motionless relative to the handpiece, and means to move the braking contact means away from contact with the turbine.

6. The structure of claim 5 wherein the braking mechanism includes a rubber bladder with a heel located in a tubular extension of the handpiece.

7. The structure of claim 5 wherein the braking mechanism includes a locking lever located in a tubular extension of the handpiece adapted to be moved by a finger.

8. The structure of claim 5 wherein the braking mechanism includes a locking pin and a spring located in a tubular extension of the handpiece adapted to be moved by a finger.

9. The structure of claim 1 including a braking mechanism with means to be attached to the tube permitting tube rotation in one direction but preventing tube rotation in the opposite direction comprising a free-wheeling clutch.

10. The structure of claim 1 wherein the end of the secured spring comprises an arcuate segment and wherein the means to secure one end of the spring comprises an arcuate groove in the surface of the tube, the tube having a slot extending into the arcuate groove, so that the arcuate spring segment can extend into the arcuate groove of the tube.

11. In a dental handpiece for use with a rotary dental instrument having a cylindrical shank: a freely rotatable means including an instrument tube to receive the instrument shank; the instrument tube comprising a freely rotatably member into which the shank can be inserted; means in the tube adapted to grip the shank to cause the instrument to rotate with the tube when the tube is rotated in one direction, the said means enabling the shank to be inserted or removed by a rotary movement relative to the tube, and braking mechanism to obstruct free movement of the freely rotatable member to enable the instrument shank to be inserted.

12. The structure of claim 11 wherein the braking mechanism includes a rubber bladder with a heel, adapted to be expanded against the freely rotatable member.

13. The strucutre of claim 11 wherein the braking mechanism includes a braking member adapted to be moved by a finger against the freely rotatable member.

14. The strucutre of claim 11 wherein the braking mechanism includes a locking pin and a spring located in the handpiece, adapted to be moved by a finger.

15. The structure of claim 11 wherein the braking mechanism comprises a free-wheeling clutch attached to the tube permitting tube rotation in one direction but preventing tube rotation in the opposite direction.

* * * * *